United States Patent [19]

Richards

[11] Patent Number: 5,043,267

[45] Date of Patent: Aug. 27, 1991

[54] METHOD FOR RAPID DETECTION OF BACTERIAL AND FUNGAL INFECTION

[75] Inventor: James C. Richards, Framingham, Mass.

[73] Assignee: E. I. du Pont de Nemours and Company, Wilmington, Del.

[21] Appl. No.: 465,404

[22] Filed: Jan. 16, 1990

Related U.S. Application Data

[63] Continuation of Ser. No. 327,409, Mar. 20, 1989, abandoned, which is a continuation of Ser. 939,003, Dec. 8, 1986, abandoned, which is a continuation-in-part of Ser. 611,588 May 18, 1984.

[51] Int. Cl.$^5$ .............................................. G01N 33/53
[52] U.S. Cl. .................................. 435/7.31; 435/7.32; 435/7.33; 435/961; 436/17; 436/174; 436/177; 436/519; 436/522
[58] Field of Search ............... 435/7, 6, 29, 270, 7.31, 435/7.32, 7.33, 961; 436/519, 522, 17, 174, 177

[56] References Cited

U.S. PATENT DOCUMENTS

| | | | |
|---|---|---|---|
| 3,883,425 | 5/1975 | Dorn | 210/23 |
| 4,131,512 | 12/1978 | Dorn | 435/7 |
| 4,358,535 | 11/1982 | Falkow et al. | 435/6 |

OTHER PUBLICATIONS

Kiehn, T. E. et al., 1983, J. Clin. Micro., 18(2):300-304.
Zierdt, C. H. et al., 1982, J. Clin. Micro., 15(1):74-77.
Zierdt, C. H., 1982, J. Clin. Micro., 15(1):172-174.
Slama, T. G. et al., 1982, Sex. Transm. Dis., 9(2):70-73.
Cohn, Z. A., 1963, J. Exp. Med., 117:27-42.
Friedlander, A. M., 1978, Inf. Imm., 22:148-154.
Ghuysen, J. M., 1968, Bact. Revs., 32(4):425-464.

*Primary Examiner*—Christine Nucker
*Attorney, Agent, or Firm*—George A. Frank

[57] ABSTRACT

A method for detecting pathogen infection in a host is provided. The method comprises lysing phagocytes from the host to release soluble components of the pathogen which are detected subsequently using a specific binding assay.

4 Claims, No Drawings

METHOD FOR RAPID DETECTION OF BACTERIAL AND FUNGAL INFECTION

This application is a continuation of application Ser. No. 07/327,409, filed Mar. 20, 1989, abandoned, which in turn is a continuation of application Ser. No. 06/939,003, filed Dec. 8, 1986, abandoned, which in turn is a continuation-in-part of application Ser. No. 06/611,588, filed May 18, 1984, abandoned.

TECHNICAL FIELD

The present invention relates to a rapid method for diagnosing the etiologic agent of bacterial or fungal infections in a host. The method involves the disruption of phagocytes to release soluble components of phagocytosed pathogens for subsequent detection in a specific binding assay.

BACKGROUND ART

Diagnosis of infection frequently involves a determination of the causative pathogen. In the case of bacterial infection, a knowledge of the pathogen can lead to an informed choice of antibiotic.

Numerous methods have been devised for clinical diagnosis. Among these are culture techniques, immunoassay, microscopy, analytical chemistry and nucleic acid hybridization.

By far, the most widely used method is culture, which involves inoculating a nutrient medium with a sample and then determining the extent of organism growth. Culture techniques are time consuming and are restricted in that they are capable of revealing the presence of only live organisms. Successful diagnosis relies upon selecting the appropriate culture media and conditions which will foster the growth of the etiologic agent. Fastidious organisms such as Mycoplasma spp., Neisseria spp., Haemophilus spp., and all obligate anaerobic organisms for example, require extraordinary culture conditions and extended periods of time to grow. If appropriate growth conditions are not met, these fastidious etiologic agents are likely to be missed when subjected to standard culture screening procedures.

Immunoassay, while promising the potential for rapidity of diagnosis, frequently lacks the sensitivity required to detect microorganisms which, during 30 to 50% of all septicemia, are present at less than or equal to one colony forming unit (CFU) per milli-liter of blood. [Kiehn, T. E. et al., J. Clin. Micro. 18, 300-304 (1983).]

Microscopy, analytical, chemical and hybridization methods frequently require sophisticated instrumentation and sample preparation and are therefore quite labor intensive.

It is known that phagocytes engulf numerous microbial pathogens. Some organisms reside within the phagocytes as intracellular parasites, while others are at a minimum, rendered nonviable by the internal degradative process of the phagocyte and, at a maximum, digested by these degradative processes.

Zierdt et al. have shown that lysis-filtration blood culture was a more sensitive culture technique than a non-lysis blood culture technique for the detection of pathogenic bacteria during septicemia in rabbits. The authors postulate that the lyses solution (a mixture of Tween-20 and Rhozyme) lyses phagocytes, thereby releasing engulfed pathogens whose viability has not been destroyed by the internal degradative processes of the phagocyte. These authors detected the presence of pathogens using conventional culture techniques. [Zierdt et al., J. Clin. Micro., 15, 74-77 (1982).] These conventional techniques can, however, only detect viable organisms not soluble products of phagocytic degradation.

The lysing solution used by Zierdt et al. is a mixture of a mild, nonionic detergent (Tween-20), and a protease including some lipase and nuclease (Rhozyme). [Zierdt, J. Clin. Micro., 15, 172-174 (1982). ]

While the lysing solution used by Zierdt et al. does lyse phagocytes to release viable pathogens for subsequent culturing, the presence of protease and nuclease in the lysing solution could present problems in other detection systems such as immunoassay or nucleic acid hybridization. It might be expected that these degradative enzymes would destroy the specific reagents required. Similarly, the degradation enzymes of the phagocyte are also released by lysis and are another source of potential degradation of the specific detection reagents.

According to Zierdt et al., the release of viable pathogen from phagocytes is desirable because the total number of viable organisms available for growth in a culture-based detection system increases.

Slama, T. G. et al. reported that the Gc2 polysaccharide derived from lipopolysaccharide of *N. gonorrhoeae* cell wall antigens was immunochemically detectable in PMN-containing fluids 2 to 6 hours after the bacterial cells had been phagocytized. Since unlysed PNM were used, the lipopolysaccharide detected was external to the PMN and there is no report by the authors of lysis of the PMN to increase the concentration of the antigens to be detected. After 24 hours, the same PMN-containing fluids did not react with specific antisera. Attempts to culture the bacteria from PMN-containing fluids 6 hours after phagocytosis indicated that the fluids were sterile. Results showed that both culture and immunochemical techniques for assay of *N. gonorrhoeae* using PMN-containing fluids with intact PMN cells were applicable, but only on a transient basis over a relatively short period. [Slama, T. G. et al., Sex Transm Dis., 9, 70-73 (1982).]

Friedlander, Infection and Immunity, Volume 22, 148-154 (1978), reports an assay for measurement of microbial killing by phagocytes. This method assumes that release of soluble radioactively labelled DNA from the microbe is direct evidence of cell death. As noted by Friedlander, since the standard assay condition did not include lysis of the phagocytes, all radioactivity detected must have been external to the phagocytes. When the phagocytes were lysed prior to testing for soluble radioactivity, no additional radioactivity was detected. This indicated that the soluble degraded DNA did not accumulate in the phagocytes, but rather was immediately released.

Richards et al., U.S. Pat. No. 4,581,331, issued Apr. 8, 1986, report a method for detection of virus or viral antigens by lysing phagocytes, separating the soluble fraction containing the virus or viral antigen and then detecting the virus or viral antigen. The only specific lytic agent reported is purified saponin. Detector systems reported include tissue culture, immunoassay and nucleic acid hybridization.

It has been found that phagocyte lysates yielding nonviable products of pathogens subjected to the internal degradative processes of the phagocytes can be used to advantage in clinical diagnosis if one uses an immunoassay or hybridization based pathogen detection system rather than a culture based detection system. The degradative processes of the phagocyte have been found in at least two examples not to degrade antigens to the point where they can no longer be recognized by their complementary antibodies.

DISCLOSURE OF THE INVENTION

The present invention is a method for detecting the presence of a bacterial or fungal pathogen in a host, which pathogen is phagocytosed and subject to at least partial degradation by phagocytes of the host, comprising:
(1) isolating from the host a test sample comprising a cellular population which comprises phagocytes;
(2) contacting the population with saponin capable of rupturing the phagocytes to release at least one soluble component of the pathogen, but incapable of rupturing unphagocytosed pathogen;
(3) separating at least one soluble component of the degraded pathogen from unphagocytosed pathogen;
(4) contacting the soluble component with a biospecific binding partner therefor; and
(5) measuring the extent of binding.

DETAILED DESCRIPTION OF THE INVENTION

The present invention is applicable for the diagnosis of many bacterial and fungal infections in man and other mammals. The method should be useful in both human and veterinary medicine. Bacteria and fungi which can be detected by the present method are those which are both phagocytosed and at least partially degraded in the phagocyte. Many clinically significant pathogens fall within this group. Generally, the gram positive and gram negative bacteria can be detected. Specifically, gram positive bacteria belonging to the genera Staphylococcus, Streptococcus, Listeria, Clostridium, and Corynebacteria can be detected. Gram negative bacteria belonging to the family Enterobacteriaceae can be detected. Gram negative bacteria belonging to the genera Haemophilus, Bacteroides, Pseudomonas, Neisseria, and Legionella can be detected. Fungi belonging to the genera Candida, Cryptococcus, Coccidiodes and Histoplasma can be detected. Bacteria and fungi belonging to these various families and genera are known to be phagocytosed by phagocytes which comprise polymorphonuclear leukocytes (PMN), monocytes and tissue macrophages. With the passage of time, the pathogen is increasingly degraded by the phagolysosomal system. The degree and rate of phagolysosomal degradation varies depending upon the age of the organism and the nature of the pathogen. This degradative process causes the removal of characteristic surface structure components of the pathogen such as pili from Neisseria, capsular polysaccharides from *Streptococcus pneumoniae*, and lipoteichoic acid which is found in virtually all gram positive bacteria. As the degradative process continues, microbial cell wall and membrane integrity are altered by the action of PMN-specific degradative processes and microbial-specific autolysins. Once the innermost cell membrane is ruptured, intracellular components of the pathogen such as DNA and RNA will be released. Once those intracellular components are released, the degradative enzymes of the phagocyte begin to destroy those components also.

Cellular populations which are suitable for practicing the present invention include blood, urine, spinal fluid, synovial fluid, mucosal secretions and scrapings, etc. Blood-containing PMN's is preferred. The principal criterion for choosing a population is that it contain phagocytes.

The cellular population is contacted with a lytic agent having the ability to rupture the phagocytes, but not having the ability to rupture unphagocytosed pathogen. In this way, the whole, viable pathogen, whether released from a PMN or free in the medium, will be available for culture-based detection to confirm the presumptive result of the more rapid soluble component-binding assay detection scheme of the present invention. Suitable lytic agents include Tween-20, a mild nonionic surfactant having an HLA index of less than 15, and the sapogenin glycosides particularly in purified form such as saponin, described by Dorn in U.S. Pat. No. 3,883,425, issued May 13, 1975, which is incorporated herein by reference. It is imperative that harsh treatments such as heat, proteolytic enzymes, strong reducing agents, strong acids and bases be avoided, in that they may not only kill viable pathogen, but may also denature the soluble pathogen components resulting from the phagocytic degradative process, making these components unrecognizable by their biospecific binding partners which include antibodies and nucleic acids.

The soluble pathogen components which result from phagocyte degradation of the intact pathogen include various chemical species which are unique to either the pathogen or a taxonomic group of which the pathogen is a member. Specific examples of soluble components and their relevance to diagnosis of microorganism presence appear in Table 1.

TABLE 1

| Chemical Composition of Gram-positive and Gram-negative Microorganisms | | |
|---|---|---|
| Polymer | Gram-positive | Gram-negative |
| Peptidoglycan* | − | − |
| Teichoic acid* and/or teichuronic acid* | − | − |
| Lipopolysaccharide* | | − |
| Lipoprotein | − | − |
| Phospholipid | − | − |
| Protein | +/− | − |
| Polysaccharide | −/− | |

*Macromolecules found only in prokaryotic organisms.
[Ghuysen, Jean-Marie. "Use of Bacteriolytic Enzymes in Determination of Wall Structure and their Role in Cell Metabolism" in Bacteriological Reviews 32:425-464, 1968.]

Soluble components can be operationally defined as those pathogen specific components which are not sedimented into a pellet fraction when subjected to a centrifugal field sufficient to pellet whole pathogens.

The soluble components are contacted with a biospecific binding partner for the component. Most often, the binding partner will be an antibody. If the soluble component is a nucleic acid (either DNA or RNA), the binding partner will be a nucleic acid having complementary base pairs.

The extent to which the soluble component binds to its biospecific binding partner can be determined by a variety of ways which are well known. For anti-body-base systems, a variety of immunoassays can be used, e.g., radioimmunoassay, enzyme-linked immunosorbent assay, radial immune diffusion, complement fixation, and others, as described in "Immunoserology in the Diagnosis of Infectious Diseases" Friedman, H. et al.

(eds.) University Park Press (Baltimore). 1979, pp 1 to 76, incorporated herein by reference. For nucleic acid detection, hybridization systems such as that described in U.S. Pat. No. 4,358,535, issued to Falkow on Nov. 9, 1982 can be used.

Surprisingly, the intracellular lysosomal enzymes, such as proteases, lipases, and nucleases that are released upon lysis of professional phagocytes, do not interfere with the method of this invention by inactivating biospecific binding partners.

It was also surprising that the soluble components to be detected accumulated in the phagocyte to an extent that allowed detection by non-culture methods. Contrary to the finding of Friedlander, it was found that these soluble components were not immediately released from the phagocyte but required approximately 8 hours for the release of the soluble components. The advantage of the present invention is that the soluble components can be detected using lysed phagocytes and immunoassay as early as 1 hour after inoculation whereas, with unlysed phagocytes, 8 hours are required and, with culture method, generally more than 18 hours are required.

These surprising advantages are a result of the process of this invention meeting the requirements that the organisms be rapidly inactivated (greater than 99% killing in two hours), the soluble components not be completely degraded rapidly, and that these components accumulate in the phagocytes to levels which can be detected by non-culture methods.

Because the present method disrupts phagocytes to release soluble pathogen components without affecting viability of unphagocytosed pathogen, a test sample can be separated, preferably by centrifugation, after the cell population is contacted with the lytic agent, into two phases: one containing insoluble, viable pathogen and the other containing soluble components. A fractional aliquot of each phase can then be tested. The soluble components can be detected in accordance with the present invention, while the insoluble components (whole, viable pathogen) can be added to nutrient media which is examined for growth. In this way, the traditional culture-based technique can be used to confirm the more rapid technique which constitutes the present invention. Conveniently, separation into the two phases can be accomplished using the tube described by Dorn in U.S. Pat. No. 4,131,512, issued Dec. 26, 1978, which is sold by the Du Pont Company under the name ISOLATOR TM.

An alternative procedure which can be used with the method of the present invention, especially in examining pediatric samples which generally provide lower volumes of sample, is to contact sample with lysing agent for a specified period of time, followed directly by both culture and specific binding assays with no additional sample processing.

The invention is illustrated by the following examples which compare traditional culture based techniques with the method of the present invention for the detection of peptidoglycan, a component of *Staphylococcus epidermidis*, and lipoteichoic acid, a component of *Streptococcus faecalis*.

EXAMPLE 1

Monoclonal antibody was prepared using purified peptidoglycan as the antigen. Peptidoglycan is known to be the major cell wall structural component of most bacteria. Peptidoglycan is a longchain mucopolysaccharide comprising alternating units of N-acetylglucosamine (NAG) and N-acetylmuramic acid (NAM) joined by $\beta-(1\rightarrow 4)$ linkages. They are known to include both short peptide chains containing D- and L-amino acids which are attached to lactyl side groups of some NAM residues. The mucopolysaccharide chains are linked together by covalent bonds between these peptide segments. The network of highly crosslinked chains is termed a sacculus.

Antibody produced by various hybridomas was screened for the ability to bind to peptidoglycan. Immunoglobulin from several hybridoma cell lines which bound specifically with peptidoglycan was purified and used in a sandwich immunoassay as follows: Anti-peptidoglycan antibody ($\alpha$-pg) was bound to latex particles. Whole bacteria known to contain peptidoglycan (pg) in their cell walls, e.g., *Staphylococcus aureus* or *Escherichia coli*, were incubated in the presence of $\alpha$-pg-latex particles. After a 2 hour incubation, unbound bacteria were washed away. Next, $\alpha$-pg conjugated to $\beta$-galactosidase ($\beta$-gal) was added to the latex particles. After a 2 hour incubation, unbound $\alpha$-pg-$\beta$-gal was washed away. Finally, O-nitrophenyl$\beta$-D-galactopyranoside (ONPG), a substrate for $\beta$-gal, was added, and optical density at 410 nm was measured. The results indicated that $10^5$ to $10^6$ whole bacteria was the minimum detection limit of the assay. This sensitivity is comparable to that of direct microscopic examination.

Other immunoassay formats were investigated: fluorescent antibody detection of whole bacteria; ELISA in which whole bacteria were bound to the wall of a microtiter plate followed by mouse $\alpha$-pg followed by labeled goat anti-mouse IgG; ELISA in which $\alpha$-pg was bound to the wall of a microtiter plate followed by bacteria followed by labeled $\alpha$-pg. None of these alternate immunoassay formats resulted in improved sensitivity.

Multiple ten milliliter aliquots of whole blood were withdrawn from a patient known to have bacteremia at a concentration of about 58 colony forming units (CFU) of *Staphylococcus epidermidis* per milliliter of blood. The blood samples were analyzed by both conventional techniques and by the method which constitutes the present invention.

One 10 mL aliquot of blood was placed into a vented blood culture bottle containing 50 mL of trypticase soy broth (TSB). TSB is essentially isotonic and does not lyse erythrocytes or phagocytes. This procedure is known to promote the growth of bacteria. At various times following the addition of blood to the broth, aliquots were removed and tested for the presence of bacteria using the immunoassay formats described above. After about a 12 hour incubation at 35° C., bacteria were detected in the immunoassays. However, bacteria could also be detected at this time by both visual examination and direct microscopic examination of the broth.

A second 10 mL aliquot of blood was placed into the lysis-centrifugation device described in U.S. Pat. No. 4,131,512, issued to Dorn on Dec. 26, 1978. The blood sample was centrifuged, and the topmost 8.5 mL of supernatant fluid was removed and maintained at 4° C. The remaining fluid, containing pelleted microorganisms, was vigorously agitated to produce a suspension referred to hereinafter as the microbial concentrate. Approximately 1 mL of the microbial concentrate was plated directly onto agar enriched growth medium. The remaining 0.5 mL of microbial concentrate was placed into 10 mL of buffered saline, and bacteria were centrifuged at 3000 rpm for fifteen minutes in a Du Pont Sorvall RT-6000 refrigerated centrifuge using an H-1000 rotor. The supernatant fluid was decanted and discarded. The pellet was tested for the presence of bacteria by the immunoassay formats described above and by light microscopy at 400× and 1000×. No bacteria were detected by any of the tests. However, after a twelve hour growth period, small colonies of bacteria were visible on the medium. The results were comparable to those obtained by broth culture. The 8.5 mL supernatant fluid described above was tested for the presence of bacteria. No bacteria were detected by either growth on nutrient medium or by direct microscopic examination. However, immunoassay was positive for peptidoglycan.

Plasma derived from the blood of the bacteremic patient was also examined. Bacterial culture, direct microscopy and immunoassay for pg were all negative.

To test the hypothesis that the presence of pg in the supernatant fluid of the lysis-centrifugation device resulted from the action of phagocytes (e.g. PMN's) on whole bacteria, an in vitro model system was constructed. PMN's were obtained from fresh human peripheral blood. *S. epidermidis* was added to the PMN cells at a concentration of $10^4$ CFU/mL, a concentration which is not detectable routinely by any of the nonculture-based techniques described previously, i.e. immunoassay and direct microscopy. At various times following the addition of *S. epidermidis*, fractional aliquots of the PMN/bacteria mixture were removed and tested for bacteria by culture plating, direct microscopy and immunoassay. In addition, fractional aliquots were placed in the lysis-centrifugation device. Culture results (24 hours after plating) indicated greater than 90% of bacteria were killed by PMN's within the first hour after the bacteria were exposed to the PMN's, while after two hours, greater than 99% killing was observed. After searching many microscopic fields at 400× or 1000×, direct fluorescent microscopy (acridine orange stain) revealed only occasionally a single fluorescent bacterium. Immunoassay results from specimens analyzed directly from the unlysed PMN/bacteria mixture were negative until approximately 8 hours when positive results were obtained. The immunoassay results on supernatant fluid specimens obtained from the lysis-centrifugation device (the lysed fraction) indicated the presence of pg only one hour after the bacteria were mixed with the PMN's. The concentration of pg increased linearly for 12 hours. Centrifugation of the lysis-centrifugation supernatant fluids prior to immunoassay did not significantly alter the immunoassay results. This indicated that the soluble antigen accumulated in the phagocyte to allow detection by immunoassay. The long period (greater than 12 hours) showing increasing antigen concentration indicates the relative insensitivity of the method of this invention to the practical problems of sample processing delays in the clinical laboratory.

EXAMPLE 2

The procedures of Example 1 were repeated using monoclonal antibody prepared using purified lipoteichoic acid (LTA) obtained from *Streptococcus faecalis* as the antigen.

The polyglycerolphosphate structural backbone of lipoteichoic acid was used to screen monoclonal antibodies for their ability to agglutinate Gram-positive bacteria known to possess LTA on or near the cell surface. Antibodies specific for the polyglycerolphosphate portion of LTA were further selected based upon the ability of deacylated cardiolipin to inhibit the agglutination of LTA-containing bacteria by the monoclonal antibodies. This inhibition indicated that the monoclonal antibodies so selected had specificity for epitopes or binding sites associated with the structural backbone and not for epitopes at or near LTA termini. This selection provides antibodies having a greater probability of maintaining reactivity with bacterial LTA after PMN degradation, since lysosomal enzymes are more typically exohydrolases that degrade terminal linkages. Essentially the same results as those obtained in Example 1 were demonstrated: the minimum detection limit with bacterial cells known to contain lipoteichoic acid was on the order of $10^5$ to $10^6$ bacterial cells. A comparison of culture-based detection and immunodetection of lipoteichoic acid obtained from lysed-PMN supernatant fluids indicated that immunodetection of lipoteichoic acid was the more sensitive technique. Bacterial antigen presence was detected by immunoassay at least 8 hours before any visible growth could be seen in culture. Moreover, lysed PMN supernatants were immunopositive, whereas equal volumes of unlysed PMN-containing blood samples were immunonegative. Therefore, analogous experimentation with both peptidoglycan and lipoteichoic acid monoclonal antibody reagents achieved essentially the same results.

Examples 1 and 2 both demonstrate that the method according to the present invention is capable of producing reliable, clinically significant results in substantially less time than traditional culture based detection systems.

I claim:

1. A method for detecting the presence of a bacterial or fungal pathogen in a host, which pathogen is phagocytosed and subject to at least partial degradation by phagocytes of the host, comprising:
   (1) isolating from the host a blood sample comprising a cellular population which comprises phagocytes;
   (2) contacting the population with saponin capable of rupturing the phogocytes to release at least one soluble antibody of a phagocytosed bacterial or fungal pathogen but incapable of rupturing unphagocytosed pathogen;
   (3) separating at least one soluble antibody of the degraded pathogen from unphagocytosed pathogen by centrifugation;
   (4) contacting the soluble antibody in the supernatant fluid with a biospecific binding partner therefor; and
   (5) measuring the extent of binding.

2. The method of claim 1 wherein the phagocyte is a polymorphonuclear leukocyte.

3. The method of claim 1 wherein the pathogen is *Staphylococcus epidermidis*, the phagocyte is a polymorphonuclear leukocyte, the soluble antigen is peptidoglycan and the antibody is a monoclonal anti-peptidoglycan antibody.

4. The method of claim 1 wherein the pathogen is *Streptococcus faecalis*, the phagocyte is a polymorphonuclear leukocyte, the soluble component is lipoteichoic acid and the biospecific binding partner is a monoclonal anti-lipoteichoic antibody.

* * * * *

UNITED STATES PATENT AND TRADEMARK OFFICE
CERTIFICATE OF CORRECTION

PATENT NO. : 5,043,267
DATED : August 27, 1991
INVENTOR(S) : James Carlton Richards It is certified that error appears in the above-identified patent and that said Letters Patent is hereby corrected as shown below:

| Column | Line | |
|---|---|---|
| 8 | 45 | "antibody" should be --antigen-- |
| 8 | 48 | "antibody" should be --antigen-- |
| 8 | 51 | "antibody" should be --antigen-- |
| 8 | 52 | "biospecific binding partner" should be --antibody-- |
| 8 | 64 | "component" should be --antigen-- |

Signed and Sealed this

Twenty-ninth Day of December, 1992

*Attest:*

DOUGLAS B. COMER

*Attesting Officer*  *Acting Commissioner of Patents and Trademarks*